(12) United States Patent
Albrecht et al.

(10) Patent No.: US 8,858,989 B2
(45) Date of Patent: Oct. 14, 2014

(54) GEL-FORMULATIONS OF HYDROPHOBIC PHOTOSENSITIZERS FOR MUCOSAL APPLICATIONS

(75) Inventors: Volker Albrecht, Jena (DE); Dietrich Scheglmann, Jena (DE)

(73) Assignee: Biolitec Pharma Marketing Ltd, F.T. Labuan (MY)

( * ) Notice: Subject to any disclaimer, the term of this patent is extended or adjusted under 35 U.S.C. 154(b) by 0 days.

(21) Appl. No.: 12/226,895

(22) PCT Filed: May 16, 2007

(86) PCT No.: PCT/US2007/011676
§ 371 (c)(1), (2), (4) Date: Oct. 31, 2008

(87) PCT Pub. No.: WO2007/136633
PCT Pub. Date: Nov. 29, 2007

(65) Prior Publication Data
US 2009/0169611 A1    Jul. 2, 2009

Related U.S. Application Data

(60) Provisional application No. 60/801,493, filed on May 18, 2006.

(51) Int. Cl.
*A61K 9/127* (2006.01)
*A61K 41/00* (2006.01)

(52) U.S. Cl.
CPC ........... *A61K 9/1271* (2013.01); *A61K 41/0071* (2013.01)
USPC ....................................... 424/450

(58) Field of Classification Search
None
See application file for complete search history.

(56) References Cited

U.S. PATENT DOCUMENTS

2002/0061330 A1* 5/2002 Chowdhary et al. .......... 424/450
2002/0156062 A1* 10/2002 Boch et al. ................... 514/185

OTHER PUBLICATIONS

Bocho, A. et al., "Characterization of a new ocular delivery system based on a dispersion of liposomes in a thermosensitive gel", International J. of Pharmaceutics, 1998, vol. 162: pp. 119-127.*
"Poloxamer" definition, downloaded Oct. 23, 2010, Wikipedia entry, one page.*

* cited by examiner

*Primary Examiner* — Michael Burkhart
(74) *Attorney, Agent, or Firm* — Bolesh J. Skutnik; B J Associates

(57) ABSTRACT

The present invention relates to improved methods of formulations of hydrophobic photosensitizers, and their precursors, for mucosal administration. The formulation of the invention comprises of hydrophobic photosensitizers which have been incorporated into suitably sized liposomes. Additionally, these formulations include the incorporation of PS-loaded liposomes into a copolymer matrix. The liposome of the present invention allows the hydrophobic photosensitizers to be incorporated into the thermogel matrix and thus promoting intimate contact between the formulation and the mucosal layer for enhanced drug absorption.

15 Claims, 2 Drawing Sheets

GEL-FORMULATIONS OF HYDROPHOBIC PHOTOSENSITIZERS FOR MUCOSAL APPLICATIONS

DOMESTIC PRIORITY UNDER 35 USC 119(e)

This application claims the benefit of U.S. Provisional Application Ser. No. 60/801,493 filed May 18, 2006, and U.S. Ser. No. 11/800,599 filed on May 7, 2007, both of which are incorporated by reference herein.

BACKGROUND OF THE INVENTION

1. Field of the invention

The invention relates to pharmaceutical composition useful in photodynamic therapy (PDT). In particular, it relates to methods of packaging a hydrophobic photosensitizer (PS) and PS precursors into copolymer liposome formulation to facilitate mucosal uptake of the drug.

2. Information Disclosure Statement

For an effective drug treatment it is important to maintain the drug concentration for a certain period of time at the absorption site and thereby facilitate the uptake of the drug. Drug applied to the mucosal layer (i.e. covering the mucosal epithelial surface) undergoes fast elimination due to the effective clearance mechanism seen in these parts of the body, thus reducing the duration of the therapeutic effect and hence requiring frequent application. When frequent dosing is required, it can result in increased costs and may lead to decreased patient compliance. In an effort to overcome these shortcomings, researchers have looked at improving the delivery systems of pharmaceutical substances. Thus a suitable drug carrier with mucoadhesive properties can improve the effectiveness of drug transfer at the absorption site.

Mucoadhesive drug delivery systems are using the attraction between mucosa cells and the polymeric drug carrier. They provide localization of the drug at the specific body site and increase penetration efficiency of the drug. These features greatly enhance the bioavailability of drugs. Obviously, understanding of mucosa/polymer interactions in the physiological environment is essential for designing mucoadhesive delivery systems.

Drug carriers are frequently used to transport and deliver drugs through the body; they protect the drug against degradation and may extend the circulation time in the bloodstream. Normal cells can be protected from the toxic side effects of the drug, and the drug can be targeted to the site of action. Examples of such carrier are microparticles, drug-polymer conjugates, polymer micelles, liposomes and nanospheres.

Drug carriers can be used to delivery hydrophobic PS and their precursors. The medicament carrier can be composed of natural and or synthetic phospholipids which are capable of forming micelles/liposomes. Hydrophobic Photosensitizers and their precursors are insoluble in water, and therefore when administered they are absorbed by the body before being dissolved thus causing adverse side effects.

Current attempts to delivery water-insoluble substance in medicaments mostly is involve some form of encapsulation or solvent carriers other than water.

While formulating a hydrophobic composition for mucosal application, it is important to use substances which are able to solubilize hydrophobic substances stable at physiological conditions, and most of all are non-irritant to the mucosal cell layer.

Several bioadhesive drugs delivery systems based on a variety of polymers have been described in patents and in the literature. For example, U.S. Pat. No. 6,387,408 by Illum et al. describes the use of adhesive material, 'adhesin' derived from bacteria or synthetic analog of the same to combine with a drug entrapped in liposome or emulsion to provide attachment to the gastrointestinal tract. Another example in U.S. Pat. No. 6,428,813 by Akiyama et al. discloses an anti-*Helicobacter pylori* pharmaceutical agent with enhanced gastrointestinal mucosa-adherent composition to treat gastric and duodenal ulcers.

U.S. Pat. No. 6,582,720 by Inagi et al. also discusses a medicinal composition having adhering capacity to the mucosal layer of stomach and duodenum. Here the drug carrier attaches to the mucosal layer at acidic pH values. In Poly (acrylic acid) (PAA) the adhesive interaction is reduced at pH higher than 5, while mucoadhesive strength of poly (hydroxyethyl methacrylate) (PHEMA) is reduced at pH 1. U.S. Patent Application 2004/0009212 by Tsai describes a thermoresponsive mucoadhesive-carrier composition for topical delivery of PS useful in photodynamic therapy (PDT). US Patent Application 2002/0156062 by Boch et al, discloses use of water soluble microaggregates (e.g. micelles, liposome) for delivering hydrophobic (water insoluble) polypyrrolic macrocyle-based photosensitizers, however the formulation is not specific to mucosal administration.

In the field of PDT, there is a continuing need for a drug delivery system that is simple, non-toxic, chemically inert, and economical and that can easily be used for formulating different types of photosensitizers. Formulations of hydrophobic photosensitizers are required not only to maintain the drug in relatively non-aggregate form, but also to achieve effective delivery to a target site. The formulation should be stable prior to administration, while displaying effective delivery and performance at the target site.

The present invention relates to thermogel formulations of hydrophobic photosensitizers and their precursors, which are incorporated into liposomes to improve delivery of the drug to cells and tissues.

OBJECTIVES AND BRIEF SUMMARY OF THE INVENTION

It is an object of this invention to provide an improved pharmaceutical formulation for hydrophobic photosensitizer for tropical application.

It is also the object of this invention to provide an innovative formulation of hydrophobic PS which is suitable for mucosal application.

It is another objective of the present invention to incorporate hydrophobic PS and their precursors into a liposomal vesicle of suitable size thus facilitating easy transport across the mucin layer.

It is a further objective of the invention to use one or more copolymers with mucoadhesive property to improve interaction between mucosal layer and the medicament formulation.

Briefly stated, the present invention provides improved formulations of hydrophobic photosensitizers and their precursors which are suitable for mucosal administration. The formulation of the invention comprises hydrophobic photosensitizers which have been incorporated into suitably sized liposomes. Additionally, these formulations include the incorporation of PS-enclosed liposomes into a copolymer matrix. The liposome of the present invention allows the hydrophobic photosensitizers to be incorporated into a thermogel matrix and thus promotes intimate contact between the formulation and the mucosal layer for enhanced drug absorption.

DETAILED DESCRIPTION OF PREFERRED EMBODIMENTS

Figure 1:
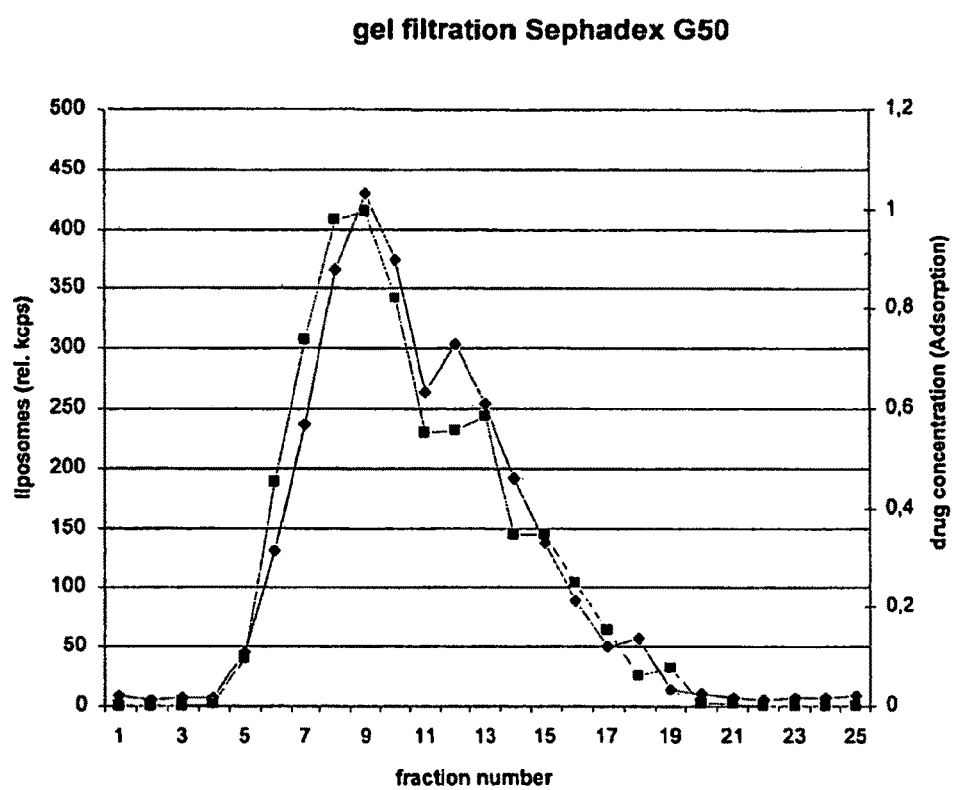
FIG. 1 is a gel filtration curve of liposomal formulated mTHPC. Both, lipid components and mTHPC show the same distribution over all fractions collected.

In this invention one or more copolymer-liposome formulations are used, to aid the delivery of highly hydrophobic drugs. An ideal formulation should be nontoxic and non-irritant to the mucosal epithelium, should be inexpensive, and should have a broad specificity for solubilizing the water insoluble, and slightly soluble pharmaceutical agents, thereby offering flexibility of application with respect to improving the bioavailability of poorly water-soluble drugs and manipulating release profiles. Thus overcoming the problems in present drug delivery systems, the described formulations of a copolymer-liposome-drug-carrier shows good mucosal adherent property and high bioavailability of the drug.

Given that the human body consists mostly of water, hydrophobic drugs are problematic when a patient's body tries to absorb them. For improving efficiency of delivery of hydrophobic PS and their precursor, one can envelope such compounds in a lipid structure termed liposome. The majority of photosensitizers of interest for PDT are hydrophobic. The tendency of highly hydrophobic photosensitizing drugs to undergo aggregation in contact with aqueous systems has a diminishing effect on the activation of the photosensitizer by light. Therefore, such drugs need to be administered in a formulation suitable to minimize aggregation in vivo.

The mucosal administration of pharmaceutical agents causes a therapeutic response only if significant dosages of the drug are enabled to permeate the absorption membrane-mucus layer. The drug permeation can be improved by using mucoadhesive polymers and permeation enhancers. The generation of novel drug formulation based on the knowledge of the absorption membrane can improve the bioavailability of mucosally applied drugs. The pharmaceutical agents mentioned above are hydrophobic photosensitizer and their precursors which are not soluble in water or are only slightly soluble in water. Delivering hydrophobic drugs to mucosal layer which is composed of 90% water as a main component requires a well designed drug formulation.

Drug delivery to the mucosal layer faces many problems as the mucosal layers are protected by effective clearance mechanisms. A drug delivery system comprising a mucoadhesive polymer can increase the contact time of the formulation at the mucosal surface thus enhancing the amount of the drug being absorbed.

The pathway by which the PS is taken up into cells depends on its chemical properties, size, charges and hydrophilic and hydrophobic properties. Furthermore, the type of the medicament carrier used for delivering the PS to the cell may also influence the intracellular accumulation and distribution. Therefore it is important to understand how these pharmaceutical compounds are internalized into the target cells.

Mucoadhesive delivery systems are able to adhere on the mucous layer covering the mucosal epithelium. These mucoadhesive properties are in many cases advantageous in order to enhance the permeation of PS through the mucosal absorption membrane by prolonging the residence time of the drug on the mucosa, which allows a sustained drug release at this site; thereby, prolonged period of drug uptake, and, subsequently a greater amount of total drug absorbed can be achieved. An intimate contact of the drug carrier to the absorption membrane can be guaranteed providing the basis for a high concentration gradient as the driving force for the drug uptake.

In one of the embodiment of the present invention an innovative formulation for hydrophobic PS and their precursor are proposed, with improved targeting ability and enhanced photodynamic activity. The hydrophobic PS and PS precursors are packaged into a suitable sized (150 nm) liposomal vesicle. The size of the liposome is important for the diffusion process across the mucous layer, hydrophobic PS-loaded liposome of large size show poor diffusion across the mucin membrane, while reducing the size improves the diffusion across the cell layer. The hydrophobic PS which is lipid soluble is incorporated into a liposome bilayer. The presence of surface ligands such as monosialoganglioside or polyoxyethylene on the liposomal surface enhances liposome stability in the physiological environment.

The mucoadhesion of polymers to the mucosa is essential for their interaction with the membrane in order to achieve a permeation enhancing effect. To serve as mucoadhesive polymer, the polymers should possess some general physiochemical features such as suitable surface property for wetting mucus/mucosal tissue surfaces and sufficient flexibility to penetrate the mucous membrane. Most efficient mucoadhesive polymers have physiochemical properties that are mostly similar to mucus substrate.

Different classes of synthetic and natural polymers have been investigated for potential use as mucoadhesives. Examples of synthetic polymers are poly (acrylic acid) (PAA), carbopol, hydroxypropyl-methylcellulose, poly (methyl-acrylate) and natural polymers like hyaluronic acid and chitosan. In some cases copolymerization is required to improve the mucoadhesive property of the polymer. The use of block copolymer at the gel surface provides more detailed control on the gel-mucosa interaction.

In this invention copolymer-liposome based formulations that offer rapid dispersion and enhanced drug absorption are proposed. These copolymer liposome formulations appear to have the ability to deliver larger amounts of pharmaceutical composition into the mucosa than do traditional lotions and creams because they provide a better reservoir for a poorly soluble drug through their capacity for enhanced solubilization. The hydrophobic drugs are successfully formulated in a block copolymer known as pluronics. Pluronics are a family of symmetrical triblock copolymers composed of polyethylene oxide (PEO) and polypropylene oxide (PPO). Pluronics are used in pharmaceutical industry for emulsification, solubilization, dispersion, and as thickening, coating and wetting agents.

The present invention is further illustrated by the following examples, but is not limited thereby.

EXAMPLE 1

Gel formulation (0.5 mg mTHPC/ml; 19% (w/w) Lutrol and water) shows high solubility of the hydrophobic drug. (m-tetrahydroxyphenylchlorin (mTHPC) also referred as Temoporfin is a hydrophobic photosensitizer):

|  | drug content ($A_{650}$ nm) | |
|---|---|---|
|  | w/o filtration | 0.2 µm filtration |
| Gel formulation (concentration 1) | 0.48 ± 0.01 | 0.49 ± 0.05 |
| Gel formulation (concentration 2) | 0.536 ± 0.013 | 0.539 ± 0.014 |

The above table value shows that no aggregation of the drug has been observed.

EXAMPLE 2

Localization of mTHPC Within the Liposomal Bilayer of the Formulation

Gel filtration of liposomal formulation performed on Sephadex G50 columns. As shown in FIG. 1, lipids and mTHPC show the same distribution over all fractions indicating a physically interaction of both components i.e. integration of mTHPC into the lipid bilayer.

EXAMPLE 3

Stability of the Gel Formulation
Particle size of liposomes is stable during thermo setting of the gel matrix as given in the table below.

|  | Particle size (nm) | polydispersitiy index |
|---|---|---|
| drug loaded gel formulation, before temperature shift to 37° C. | 142.7 ± 0.2 | 0.123 ± 0.005 |
| drug loaded gel formulation, after temperature shift to 37° C. | 141.4 ± 0.6 | 0.137 ± 0.005 |

EXAMPLE 4

Stability of the ready to use gel formulation at room temperature (drug concentration 0.5 mg/ml).

| particle size (nm) | drug (mg/ml) | storage time (days) | PI |
|---|---|---|---|
| 124 | 0.5 | 1 | 0.64 |
| 122 | 0.5 | 6 | 0.63 |
| 102 | 0.5 | 19 | 0.80 |
| 110 | 0.5 | 36 | 0.62 |
| 117 | 0.5 | 104 | 0.80 |
| 112 | 0.5 | 180 | 0.60 |
| 117 | 0.5 | 280 | 0.61 |
| 108 | 0.5 | 418 | 0.69 |
| 118 | 0.5 | 467 | 0.58 |

The particle size of the loaded formulation increased only slightly over the period of storage as observed from the table, indicating a high physical stability at the storage temperature and condition.

EXAMPLE 5

Figure 2:
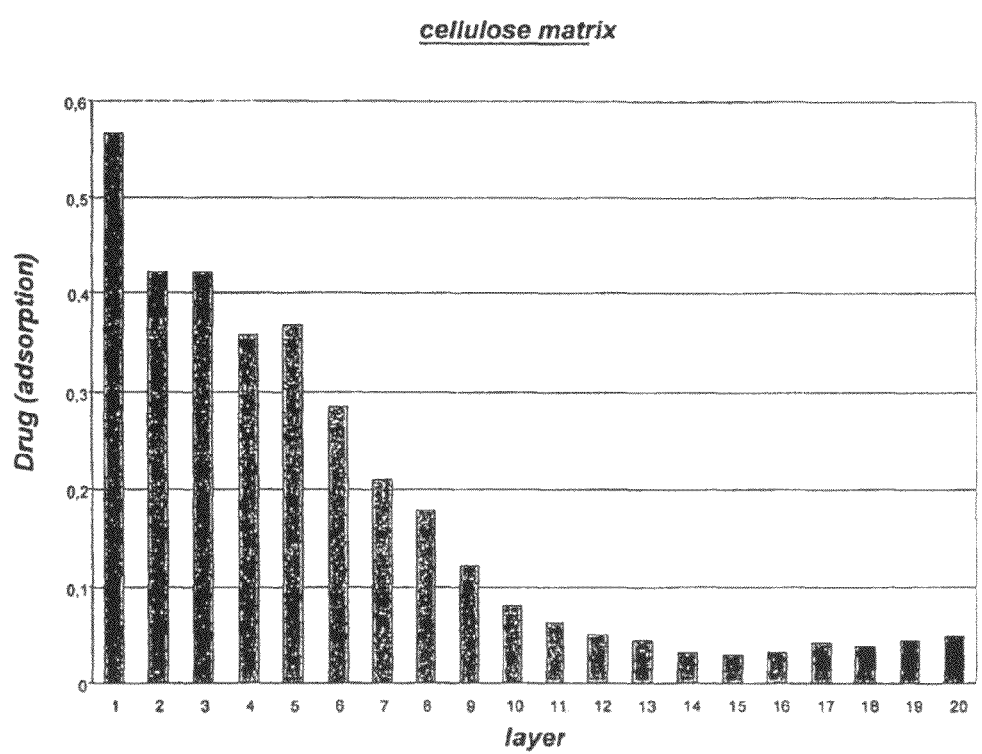
FIG. 2 depicts the penetration behavior of the gel formulation in cellulose matrix at 37° C., 100% RH.

FIG. 2 illustrates the penetration behavior of the gel formulation of mTHPC (0.5 mg drug/ml) which was administrated to cellulose matrix at 37° C., 100% RH. The drug concentrations are measured after 16 hours of incubation. Each layer represents 0.25 mm of depth and layer 1 is the site of application. From FIG. 2 it is seen that the drug penetration decreases as the number layers increases.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A chemical composition formulation for the delivery of a hydrophobic drug across a mucus coated membrane, consisting of (a) a lipid soluble, hydrophobic photosensitizer or a lipid soluble, hydrophobic photosensitizer precursor, (b) a liposomal vesicle, and (c) a mucoadhesant; wherein said liposomal vesicle is based on phospholipids and said mucoadhesant comprises at least one copolymer.

2. The chemical composition formulation according to claim 1, further including a permeation enhancer.

3. The chemical composition formulation according to claim 1, further including ligands on said liposomal vesicle.

4. The chemical composition formulation according to claim 3, wherein said ligands are monosialoganglioside or polyoxyethylene.

5. The chemical composition formulation according to claim 1, wherein said at least one copolymer is selected from the group consisting of block copolymers, poly (acrylic acid) (PAA), carbopol, hydroxypropyl-methylcellulose and poly (methyl-acrylate).

6. The chemical composition formulation according to claim 1, wherein said at least one copolymer comprises symmetrical triblock copolymers composed of polyethylene oxide (PEO) and polypropylene oxide (PPO).

7. The chemical composition formulation according to claim 1, wherein said liposomal vesicle has an initial diameter of about 150 nm or less.

8. The chemical composition formulation according to claim 1, wherein said lipid soluble, hydrophobic photosensitizer or lipid soluble, hydrophobic photosensitizer precursor is packaged into said liposomal vesicle forming loaded liposomes and said loaded liposomes are incorporated into said mucoadhesant.

9. The chemical composition formulation according to claim 8, wherein said mucoadhesant is a copolymer matrix.

10. The chemical composition formulation according to claim 9, wherein said copolymer matrix comprises at least one copolymer selected from the group consisting of block copolymers, poly (acrylic acid) (PAA), carbopol, hydroxypropyl-methylcellulose and poly (methyl-acrylate).

11. The chemical composition formulation according to claim 9, wherein said copolymer matrix comprises symmetrical triblock copolymers composed of polyethylene oxide (PEO) and polypropylene oxide (PPO).

12. The chemical composition formulation according to claim 8, wherein said liposomal vesicle has an initial diameter of about 150 nm or less.

13. The chemical composition formulation according to claim 8, further including a permeation enhancer.

14. The chemical composition formulation according to claim 8, further including ligands on said liposomal vesicle.

15. The chemical composition formulation according to claim 14, wherein said ligands are monosialoganglioside or polyoxyethylene.

* * * * *